United States Patent [19]
Christian et al.

[11] Patent Number: 6,119,511
[45] Date of Patent: Sep. 19, 2000

[54] METHOD AND APPARATUS TO MEASURE SURFACE TENSION BY INVERTED VERTICAL PULL

[75] Inventors: Sherril D. Christian, Norman; Andrew R. Slagle, Oklahoma City; Edwin E. Tucker; John F. Scamehorn, both of Norman, all of Okla.; Katsuhiko Fujio, Matsumoto, Japan

[73] Assignee: Surface Tensiometry, Inc., Norman, Okla.

[21] Appl. No.: 09/299,379

[22] Filed: Apr. 27, 1999

Related U.S. Application Data

[60] Provisional application No. 60/083,176, Apr. 27, 1998, and provisional application No. 60/091,043, Jun. 29, 1998.

[51] Int. Cl.[7] .................................................. G01N 13/02
[52] U.S. Cl. ........................................ 73/64.48; 73/64.49
[58] Field of Search ............................... 73/64.48, 64.49, 73/64.51

[56] References Cited

U.S. PATENT DOCUMENTS

| | | |
|---|---|---|
| 1,960,224 | 5/1934 | Schoenberg ................................. 73/51 |
| 3,060,727 | 10/1962 | Cortiss ......................................... 73/53 |
| 3,765,227 | 10/1973 | Campbell et al. . | 
| 3,780,569 | 12/1973 | Graham .................................... 73/64.4 |
| 4,228,677 | 10/1980 | Olsson et al. . |
| 4,361,032 | 11/1982 | Lessnig et al. . |
| 4,416,148 | 11/1983 | Klus et al. . |
| 4,527,421 | 7/1985 | Miller . |
| 5,305,632 | 4/1994 | Sprenger . |
| 5,311,768 | 5/1994 | Seib et al. .............................. 73/54.22 |

OTHER PUBLICATIONS

Sherril D. Christian et. al., "Inverted Vertical Pull Surface Tension Method", Langmuir, vol. 14, Nr. 11, pp. 3126–3128. (May 5, 1998).
Lecomte Du Nouy, P., J. Gen Physiol, 1, 521 (1919).
Harkins, W.D. and Jordan, H.F., J. Amer. Chem. Soc., 52, 1751 (1930).
Freud, D.B. and Freud, H.Z., J. Amer. Chem. Soc., 52, 1772 (1930).
Padday, J. F., J. Electroanal. Interfacial Electrochem., 37, 3113 (1972).
Padday, J. F., Pitt, A. R., and Pashley, R. M., J. Chem. Soc. Faraday Trans. 1, 71, 1919 (1974).
Couper, A., in "Physical Methods of Chemistry, 2nd Ed., vol. IXA. Investigations of Surfaces and Interfaces—Part A", (B. W. Rossiter and R. C. Baetzold), p. 1, Wiley–Interscience, New York, 1993.
Adamson, A. W. "Physical Chemistry of Surfaces.", 5th Ed., Wiley–Interscience, New York, 1990.
Zuidema, H. H., and Waters, G. W., Ind. Eng. Chem., 13(5), 312 (1941).
Furlong, D. N., and Hartland, S., Journal of the Chemical Society (United Kingdom) Faraday I, 76, 457 (1980).
Furlong, D. N., and Hartland, S., Journal of the Chemical Society (United Kingdom) Faraday I, 76, 467 (1980).

*Primary Examiner*—Hezron Williams
*Assistant Examiner*—J. David Wiggins
*Attorney, Agent, or Firm*—James F. Harvey

[57] ABSTRACT

A method and apparatus is presented for determining surface tension of a liquid or interfacial tension between two dissimilar liquids by using a rigidly suspended probe with small sample sizes and by measuring probe force using a top-loading balance used for supporting the container of liquids under test. When a small sample size in a small container is used, capillary action between a probe and the container walls enhances the measured force, and an adjustment factor for the capillary action must be applied. A probe rigidly suspended to overcome capillary action between the probe and walls permits such measurements. For any sized sample, in accordance with Isaac Newton's third law of equal and opposite forces acting between objects, the force required for lifting a probe vertically from a liquid is equivalent to the reduction in weight of the liquid and container. Force magnitude is thus determined using a top-loading balance for observing weight change, either in the liquid while a suitably configured probe is withdrawn from the liquid or in a probe suspended by a direction converter resting on a top-loading balance while the container and liquid are lowered.

21 Claims, 5 Drawing Sheets

METHOD AND APPARATUS TO MEASURE SURFACE TENSION BY INVERTED VERTICAL PULL

CROSS-REFERENCES TO RELATED APPLICATIONS

This patent application claims priority based upon the following two provisional patent applications: No. 60/083,176, filed on Apr. 27, 1998 and No. 60/091,043, filed on Jun. 29, 1998 both of the same or similar title.

BACKGROUND OF THE INVENTION

1. Field of the Invention

The invention relates to scientific measurement devices, more particularly to a method and apparatus for measuring the surface tension of a liquid or the interfacial tension between two dissimilar liquids, by measuring the reduction in weight of the sample liquid as a probe rigidly position to prevent lateral movement is vertically pulled away from the sample rather than by directly measuring the force required to pull a probe away from the sample.

2. Description of the Prior Art

Surface tension is defined as a property of liquids in which the boundary tends to contract to the smallest possible area because of unequal molecular cohesive forces near the boundary. It is measured by the force required to break an object or probe free of the boundary. This boundary may be the exposed surface of the liquid to the air or it may be between two immiscible liquids; when referring to the surface tension of the boundary between the liquid under investigation and another liquid, we use the term "interfacial tension", but for purposes of this invention, the term surface tension is assumed to include both. Surface tension is manifested by a phenomenon known in physics as the meniscus of the liquid, which is the concavity or convexity of the liquid's surface as it interacts with the probe. As a result of capillarity, the liquid's surface is concave against the probe when the probe strongly attracts the liquid, as with water, and it is convex when the liquid is more strongly attracted to itself, as with mercury.

Many methods have been proposed for measuring surface tension of a liquid and interfacial tension between two dissimilar liquids. One technique is to use maximum bubble pressure methods where a gas is passed through an orifice tube into the test liquid, forming a succession of bubbles. Since the inflation pressure inside each bubble is at a maximum when the bubble achieves minimum radius of curvature as the bubble assumes hemispherical shape at the orifice, the maximum bubble pressure is directly related to the surface tension of the liquid. However, these methods require are costly in terms of the time required to perform valid measurements. Other so called static equilibrium techniques rely on measuring the vertical force required to remove a free hanging probe (such as a plate, rod, ring, or other solid object) from a liquid as the surface tension force of the liquid resists the removal of the probe. Such measurements are performed fairly rapidly, but they methods require a minimum sample size to be effective.

All of these static equilibrium methods of measuring surface tension require that a probe be suspended above and in the same plane as the liquid(s). The probe is attached to a sensitive balance, such as a torsion balance or a microbalance, mounted above the liquid(s), so that the force exerted by the surface tension of the liquid can be measured while the probe is pulled upward or pushed downward through the plane surface of the liquid(s). The maximum required force is found prior to the probe breaking through its meniscus with the liquid, and surface tension can be calculated from this value of force.

These static equilibrium methods exhibit several disadvantages. One disadvantage is that they require expensive and sensitive analytical balancing mechanisms to measure overhead the force exerted on a suspended probe. These mechanisms are expensive, sensitive, and awkward to work with. Recently, top-loading analytical balances have been developed that automatically maintain the weighted object at the same height. These devices are more convenient to use and are less expensive than the more traditional methods of weighing probes. They use modem technologies such as piezoelectric devices or load cells to measure force without movement of the object being measured.

A second disadvantage is the delicacy of the probe used for measurement. A standard configuration for a probe is commonly called the "du Noüy ring", which consists of a wire ring of known dimensions composed of platinum-iridium alloy. The wire ring must be carefully calibrated so that the thickness of the wire forming the ring and the diameter of the ring are known precisely. The ring must be handled very carefully so as not to deform the circularity of the ring and thus adversely affect its calibration. The wire ring must be handled so as to prevent oily films from being deposited on the ring by the fingers; this affects the manner in which the ring interacts with the liquid whose surface tension is being measured. And finally, the wire ring must be constructed from special alloys, preferably platinum-iridium, which will permit the ring to be cleaned by passing it through a flame, thus burning off unwanted oils without deforming the ring through thermal stress. The same considerations apply more or less to other probe configurations, such as the Wilhelmy plate configuration. If any of the above-mentioned actions is performed carelessly, then the measurement becomes suspect and thus invalid.

A third disadvantage of the traditional measurement method is that it is ineffective for measuring relatively small liquid samples. Capillary action tends to attract the probe to the sides of the container. If the sample size is large enough whereby the probe does not directly interact with the sides of the container, then an adjustment factor must be applied to account for the volume of liquid in the meniscus between the sides of the probe and the interior walls of the container. This adjustment is accomplished by mathematical integration and is given in two articles by D. N. Furlong and S. Hartland, Journal of the Chemical Society Faraday I, vol 76, p. 457 (1980) and vol 76, p. 467 (1980). A free hanging probe is attracted to the walls of the container holding the liquid sample. For small containers and sample sizes, this capillary action of the walls of the become so severe that it invalidates the measurements since a free-hanging probe cannot be kept from contact with the container walls. This traditional method of measuring surface tension is thus not suitable for small sample sizes on the order of 0.4 mL or less.

A fourth disadvantage of traditional methods, especially for volatile liquids, is that evaporation of the liquid during the measurement process can adversely skew the measurement. Evaporation can be reduced by use of small openings through which the probe is inserted or by using small sample sizes.

Thus, traditional methods of measuring surface tension have the following disadvantages:

a. expensive balances mounted above the liquid sample are required to measure the force exerted on the probe;

b. the probe must be very carefully fabricated and handled;

c. surface tension can only be measured for relatively large sample sizes; and d. evaporation can adversely affect the measurement.

What is needed is a device for measuring surface tension which avoids the problems of excessive delicacy, expense, and sample size.

SUMMARY OF THE INVENTION

The present invention relates to a method and apparatus for determining surface tension in small sample sizes by use of rigidly fixed probes and measuring the force of surface tension by means of a top-loading balance employing a directional converter mechanism. The standard prior methods used by Wilhelmy, du Noüy, and Padday all involved directly measuring the force required to pull or push differently configured probes through the surface of the sample liquid. The inventors have observed that a necessary consequence of Newton's third law is that this traditional method for measuring surface tension, interfacial tension, and contact angle, can instead be performed indirectly by weighing the liquid(s) rather than the suspended probe. In other words, instead of measuring the force required to pull a probe away from the surface of the liquid, the reduction of weight of the liquid itself is measured as the probe is pulled vertically up and away from the liquid. In the past, changes in weight have been determined by measurements from above the liquid(s) to determine surface and interfacial forces, when plates, rods, rings, capillaries, and other objects contacted the liquid surface. By measuring the change in weight of the liquid, the mechanism of a top-loading analytical balance may be used in lieu of the more traditional torsion balance or microbalance; the inventors call this the vertical pull method. Furthermore, by using a simple direction converter, then the top-loading balance may be interchangeably used in measuring either the change in weight of the liquid or the force exerted on the probe. The method of measuring change in force exerted on a probe, which is suspended by a direction converter resting on a top-loading balance, by a liquid being moved vertically has been called the inverted pull method by the inventors.

In summary, the traditional method of deriving surface tension can be characterized by (1) motion of the probe, (2) direct measurement of the force required to move the probe, and (3) no motion of the sample. The vertical pull method of the present invention can be characterized by (1) motion of the probe and (2) measurement of the change in weight of the sample, and (3) no motion of the sample. The inverted vertical pull method of the present invention can be characterized by (1) no motion of the probe, (2) direct measurement of the force on the probe, and (3) motion of the sample. All embodiments preferably incorporate a fixed probe constrained from lateral movement and a small sample size to enhance the magnitude of the force as measured and to thus make the extremum more pronounced. However, large sample sizes measured using rigidly positioned probes can also be used with either method.

It is therefore an object of the present invention to provide an alternative method for measuring surface tensions, interfacial tensions, and contact angles of liquids at solid surfaces.

It is a further object of the present invention to provide a method for measuring surface tension, interfacial tension, and contact angle, by bringing a probe into contact with the surface of the liquid being measured, withdrawing it without breaking the meniscus, and measuring the maximum reduction in weight of the liquid thus obtained.

It is a further object of the present invention to provide an apparatus for measuring surface tension, interfacial tension, and contact angle, by measuring the reduction in weight of the liquid whose properties are being measured, instead of measuring the vertical force required to move the probe through the liquid.

It is a further object of the present invention to provide an inexpensive apparatus for measuring surface tension, interfacial tension, and contact angle.

It is a further object of this invention to reduce experimental error in measuring surface tension, interfacial tension, and contact angle, where such error is caused by careless handling of the measurement probe.

It is a further object of this invention to reduce the necessity of a large sample size of the liquid by use of a probe in the form of a rod and a liquid vessel in the form of a tube, where the diameter of the circular rod is slightly smaller than the diameter of the circular tube.

It is a further object of this invention to provide a means for using a top loading balance alternatively to measure either the weight of the liquid or the force on a probe.

It is a further object of this invention to provide a rigidly fixed probe constrained from lateral movement, as opposed to a free hanging probe, which will withstand capillary forces which would tend to attract the probe to the sides of a vessel, and will maintain its central positioning when small sample sizes, and correspondingly small vessels, are employed.

Further objects and advantages of this invention will become more readily apparent upon reference to the following detailed description of a preferred embodiment, as illustrated in the accompanying drawings.

It is to be understood that the present invention is not limited in its application to the details of construction and arrangement of parts illustrated in the accompanying drawings, since the invention is capable of other embodiments, and of being practiced or carried out in various ways within the scope of the claims. Also, it is to be understood that the phraseology and terminology employed herein is for the purpose of description and not of limitation.

DETAILED DESCRIPTION OF THE PREFERRED EMBODIMENT

Figure 1:
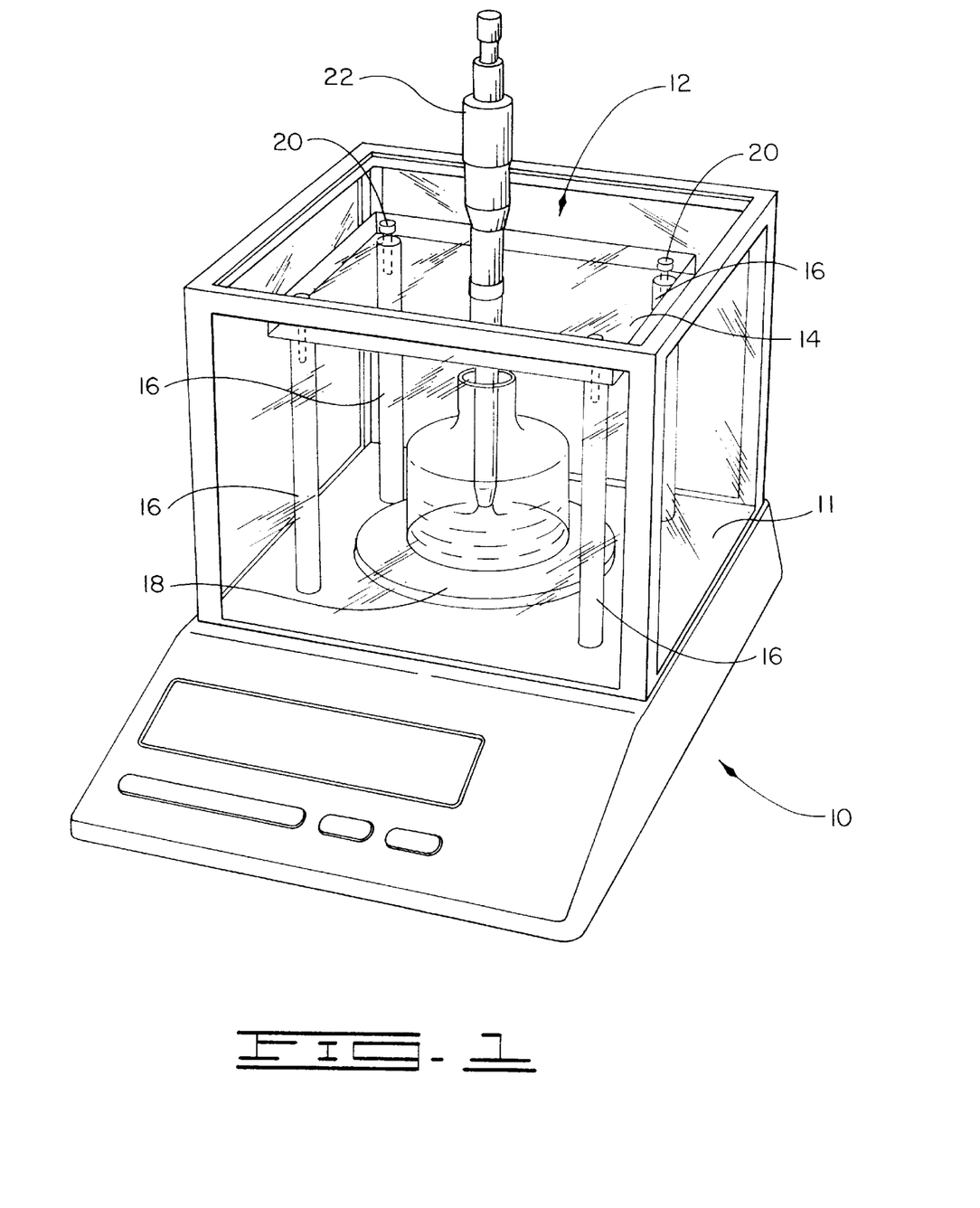
FIG. 1 shows a perspective elevation of an embodiment of the invention illustrating the vertical pull rod method.

FIG. 1 illustrates the use of the vertical pull method of measuring surface tension of a liquid. The surface tension measuring apparatus 12 consists of a generally square plate 14 supported by four equal length legs 16, secured at each corner of the plate 14 by screws 20 which position legs 16 perpendicular to plate 14 and parallel to one another. As shown, plate 14 is constructed of a piece of clear lucite approximately one-half inch thick. Although any material with suitable rigidity may be used for plate 14, a transparent material was chosen to aid adjustment and observation of the apparatus. The surface tension measuring apparatus 12 rests on the upper surface 11 of a top-loading balance 10 so that it is directly over the balance pan 18 of said balance whereby the legs 16 do not come in contact with the balance pan 18. Legs 16 are precisely cut to equal lengths so that the plate 14 is parallel to the upper surface 11 of the top-loading balance 10, so that the need for a separate spirit leveling means for the surface tension measuring apparatus 12 is eliminated. A high-quality micrometer 22 is inserted through a hole in plate 14 and firmly secured by any suitable means.

Figure 2:
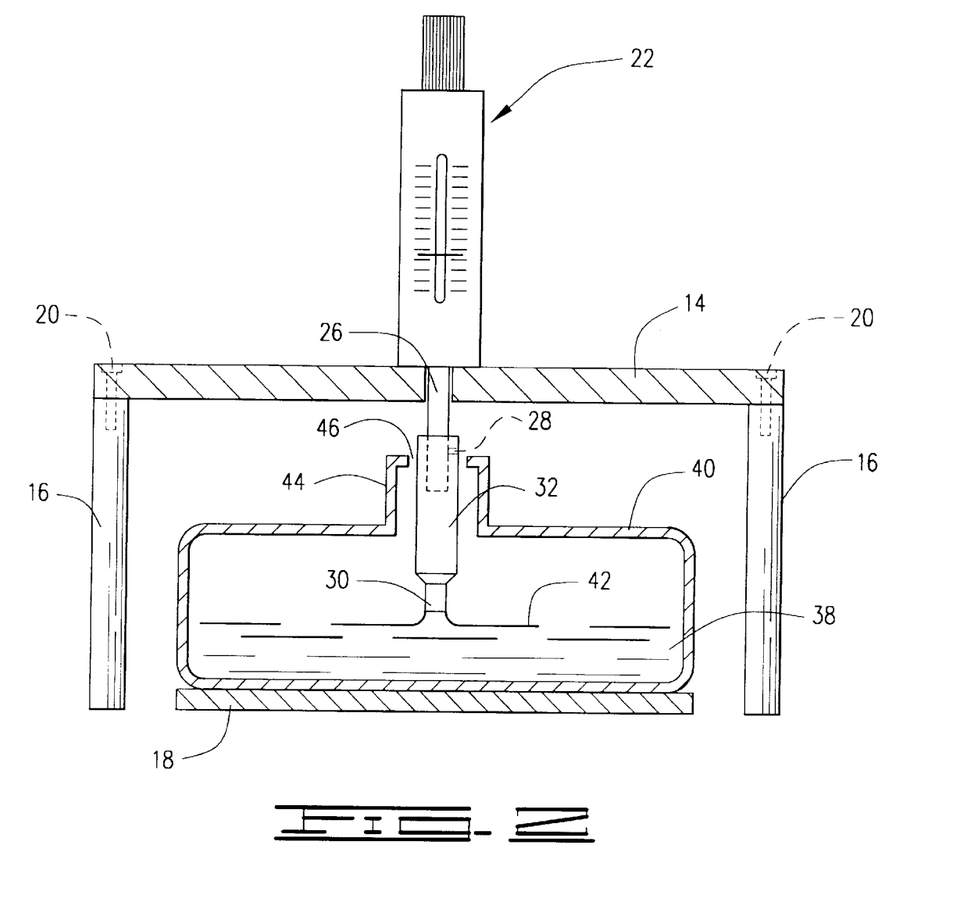
FIG. 2 shows a schematic diagram of the surface tension measuring apparatus employing the vertical pull rod method.

In FIG. 2 we see a schematic drawing which further details the interaction of the micrometer 22 and the liquid sample 38. Metal spindle 26 of micrometer 22 is removably inserted into a centrally positioned cavity in the first end of cylindrical probe 32 so that it is in close contact with the inner wall of said cavity. Metal spindle 26 is fixedly secured therein by set screw 28. The second end of the cylindrical probe 32 has a reduced diameter section 30 with a planar bottom perpendicular to the axis of the probe 32. The purpose of the micrometer 22 is to permit reproducible vertical positioning of the bottom of probe 32. Probe 32 is in the form of a rod and has a nominal radius of 3.175 mm; other radii may be used depending upon the size of the apparatus and the liquid being measured.

Figure 7:
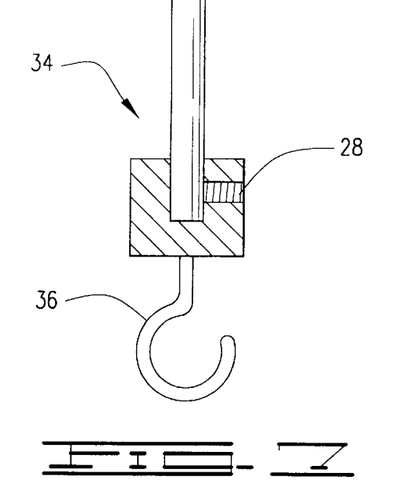
FIG. 7 shows an alternative hook attachment which can be used in place of the rigidly fixed probe so that a free hanging probe may be used.

Although probe 32 is attached to metal spindle 26 in a rigid configuration, a variety of probes can be attached to metal spindle 26 in a free swinging manner by using a hook attachment 34 as shown in FIG. 7. Hook attachment 34 receives metal spindle 26 in the same manner as probe 32 and is secured to the metal spindle 26 by set screw 28. Any appropriate probe hanging freely from hook 36 may be used, such as a du Noüy ring (not shown) or the Wilhelmy plate (not shown), both of which are well known to the art. Free swinging probes are desirable for experimentally comparing readings obtained by various methods, but as shall be seen later, the rigid attachment method shown in FIG. 2 is preferred. Probe 32 can be constructed of solid tube stock composed of an inexpensive material which is not easily deformable. A probe such as the du Noüy ring is costly, delicate, and must be of a platinum-iridium composition so that it is not deformed by heat when it is flamed in a burner to burn off oils deposited from normal handling; these oils adversely skew the measurement. Probe 32 may be flamed with ease without risk of deformation. However, because of the facial surface area and mass of the rod configuration, use of the rod-shaped probe presents a problem of buoyancy if the area of its bottom face is too large. If the area of its bottom face is too small, then insufficient force is exerted on the probe by surface tension, making the measurement process more delicate. A trade-off must be made between buoyancy and magnitude of force. However, the magnitude of force is enhanced by the use of small sample sizes as can be seen below.

As previously stated, the second end of the cylindrical probe 32 has a reduced diameter section 30 with a flat bottom perpendicular to the axis of the probe 32. This reduced diameter section 30 can be varied across a set of suitable probes with differing diameter values for section 30, thus permitting a choice of probe to be made depending upon the composition of the liquid sample 38.

Micrometer 22 is fixed to plate 14 which serves as a stable platform to hold micrometer 22 and its attached probe 32 in a rigid vertical position so that probe 32 may be lowered through the opening 46 in neck 44 of a sample cell 40 into the liquid sample 38 for which the surface tension is to be determined. Sample cell 40 is constructed of glass and has a single opening 46 for insertion of probe 32. Other materials may be used in the construction of the sample cell 40, but glass has been found to be the most universal material. Probe 32 is centrally positioned in opening 46 of neck 44, coming in close proximity to the walls of the neck 44 without contact in order to reduce loss of liquid mass through evaporation. Sample cell 40 rests on a balance pan 18 to determine the reduction of weight of the combination of liquid 38 and sample cell 40. In this embodiment, the balance pan 18 is stable in a vertical direction and does not move when weight is applied. Additional openings may also be constructed in sample cell 40 for such devices as thermometers or paddles to stir the liquid mixture.

Figure 3:
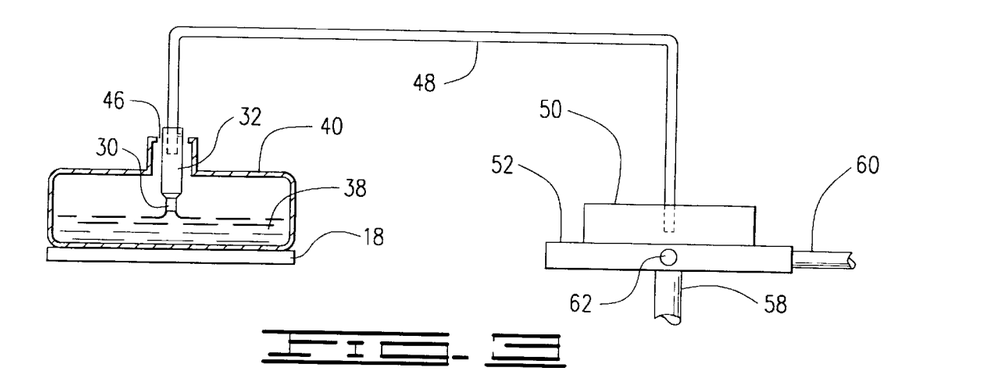
FIG. 3 shows a schematic diagram of the inverted vertical pull rod method wherein the change in weight of the sample liquid is measured.
Figure 4:
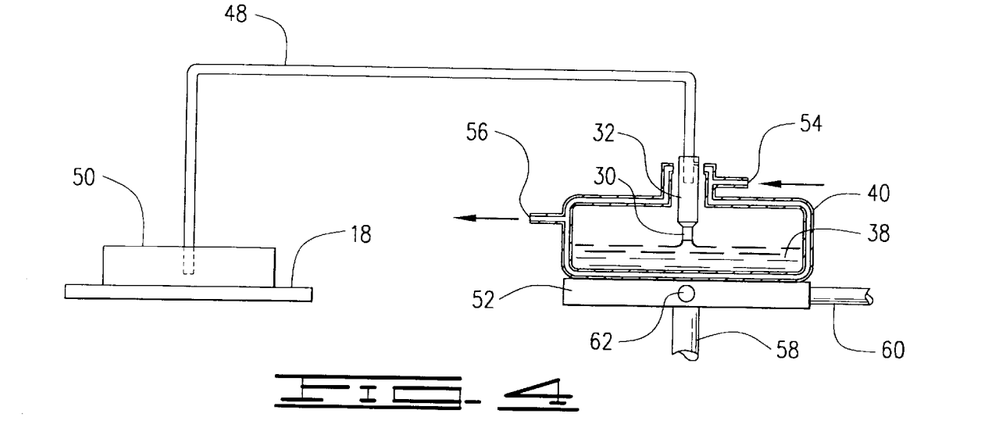
FIG. 4 shows a schematic diagram of the inverted vertical pull rod method wherein the force exerted on a rigidly fixed probe is measured using a top loading balance.
Figure 5:
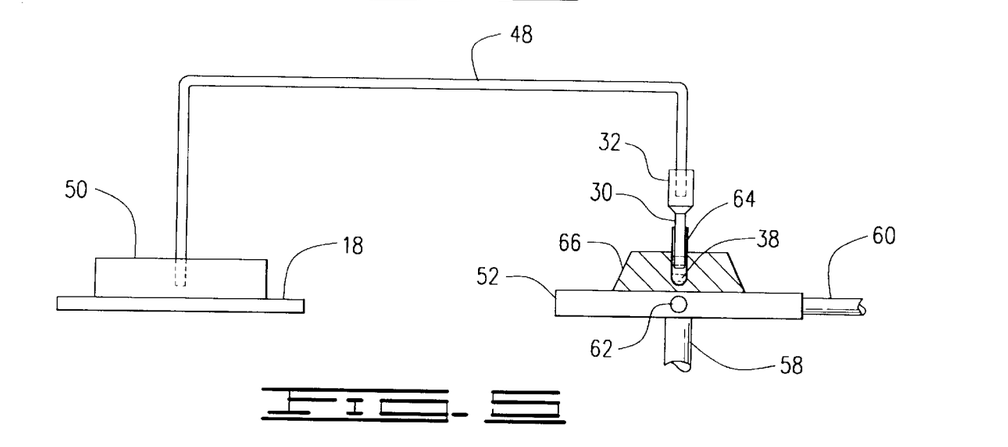
FIG. 5 shows a schematic diagram of the inverted vertical pull rod method wherein the force exerted on rigidly fixed probe is measured using a top loading balance for small samples.
Figure 6:
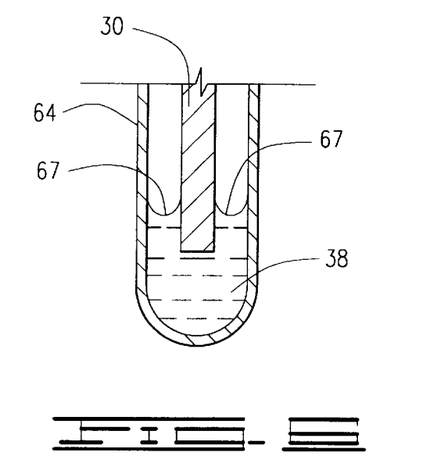
FIG. 6 shows in more detail the interaction of the meniscus of the sample liquid with both the walls of the sample vessel and the rigidly fixed probe.

FIGS. 3, 4, and 5 illustrate the inverted pull method which incorporates a directional converter arm 48 and the conceptual interchangeability of platforms, i.e. the balance pan 18 and the moveable stage 52. Referring to FIG. 3, a directional converter arm 48 is used to change the direction of vertical pull. The directional converter arm 48 is constructed of stainless steel rods or tubes (or other suitable rigid rods or tubes), attached to a support 50 that rests horizontally on a moveable stage 52. The support 50 must be sufficiently massive and have a shape that will prevent the torque exerted on directional converter arm 48 by the probe 32 and the force exerted on the probe 32 from displacing the support 50. The end of the directional converter arm 48 has a diameter suitable for fixed attachment of a variety of probes 32 for use in surface tension and interfacial tension measurements, density measurements, and other physical property measurements. Alternatively, any solid probe can be allowed to hang freely from a hook attachment 34 at the end of the directional converter arm 48, as illustrated in FIG. 7. Liquid sample 38 whose surface tension is being measured is contained in sample cell 40 which rests on a balance pan 18 of a top-loading balance. Moveable stage 52 is a rigidly fixed platform aligned so it and the balance pan 18 are coplanar. It can be micro-adjusted in three directions while maintaining alignment with the balance pan 18, i.e. vertically (z-direction) by z-adjustment means 58 and in a plane (x-direction and y-direction) by x-adjustment means 60 and y-adjustment means 62. Any suitable method known to the industry which allows adjustment in micron increments may be used to articulate the moveable stage 52, namely either manually by screws, worm gears, or micrometers (not shown) or by computerized stepper motors, linear motors, or servo mechanisms (not shown). Moveable stage 52 is used to center probe 32 within the opening of the sample cell 40 through x-y adjustment and to raise or lower probe 32 so as to bring it in contact with liquid sample 38.

Referring to FIG. 4, the configuration of FIG. 3 is reversed with support 50 resting on the balance pan 18 and sample cell 40 resting on the moveable stage 52. This configuration is a preferable embodiment to the one shown in FIG. 3 in situations when the environment of the liquid sample 38 must be controlled. In the embodiment shown, the sample cell 40 consists of a double-walled container with an inlet 54 and an outlet 56 for circulation of a temperature controlled fluid, normally water, to maintain the liquid sample 38 at a constant temperature during the surface tension measurement process. This embodiment is preferable when the liquid sample 38 must have a controlled environment and where the sensitivity or configuration of the top-loading balance interferes with such environmental considerations, although it could be used in the absence of special environmental considerations as well. Moveable stage 52 is controlled as before for centering probe 32 within the opening 46 of the sample cell 40 through x-y adjustment and for raising or lowering sample cell 40 so as to bring probe 32 in contact with liquid sample 38.

Referring to FIG. 5, the configuration of FIG. 4 is used for measuring surface tension of small samples. A small sample cell 64 having an inside radius as small as 1 to 2 mm greater than that of the circular probe 32 holds liquid sample 38, nominally with volume 0.4 mL or less, and is supported in a vertical position by small sample support 66. Since probe 32 is fixedly connected to directional converter arm 48, it resists capillary force which tends to attract it to the walls of liquid sample 38. An unanticipated and useful advantage of this embodiment for a small sample cell 64 is that the maximum weight obtained is much larger than that obtained by using the usual rod method with liquids in larger-diameter vessels. These enhanced values of the maximum weight can be obtained for probes contacting liquids contained in tubes having diameters only a factor of 1.5 to 4 greater than the probe diameters. For example, with a probe 32 which is 0.635 cm. in diameter and utilizing a pure liquid water sample with inside diameter of small sample cell 64 approximately 1.0 cm., the maximum measured weight is 0.368 g., compared to a maximum weight of only 0.242 g. when the same probe is used with liquid water in a large-diameter vessel. Changes of this magnitude are predicted theoretically. For such small samples, an adjustment, which well known to the art and referenced above, must be made to account for the volume of liquid contained in the meniscus 67 between the reduced diameter section 30 of probe 32 and the interior walls of small sample cell 64. This adjustment is mathematically significant for gaps between the probe and the sample cell of from 1 mm to approximately 2 cm. This magnification of force values obtained from smaller vessel sizes makes the determination of maximum or minimum weight value more pronounced and easier to detect.

As can be readily observed from the foregoing description of various embodiments, the rigidly fixed probe 32 used in conjunction with a small sample cell 64, so that only small samples are required for surface tension measurements, is regarded as the novel and unique inventive concept of this invention and is incorporated in the preferred embodiment. The direction converter arm, whereby probe 32 is suspended above the liquid sample 38 so that probe 32 may either be weighed from below on top-loading balance pan 18 or moved from below with moveable stage 52, is also considered to be novel and incorporated in the preferred embodiment.

Figure 9:
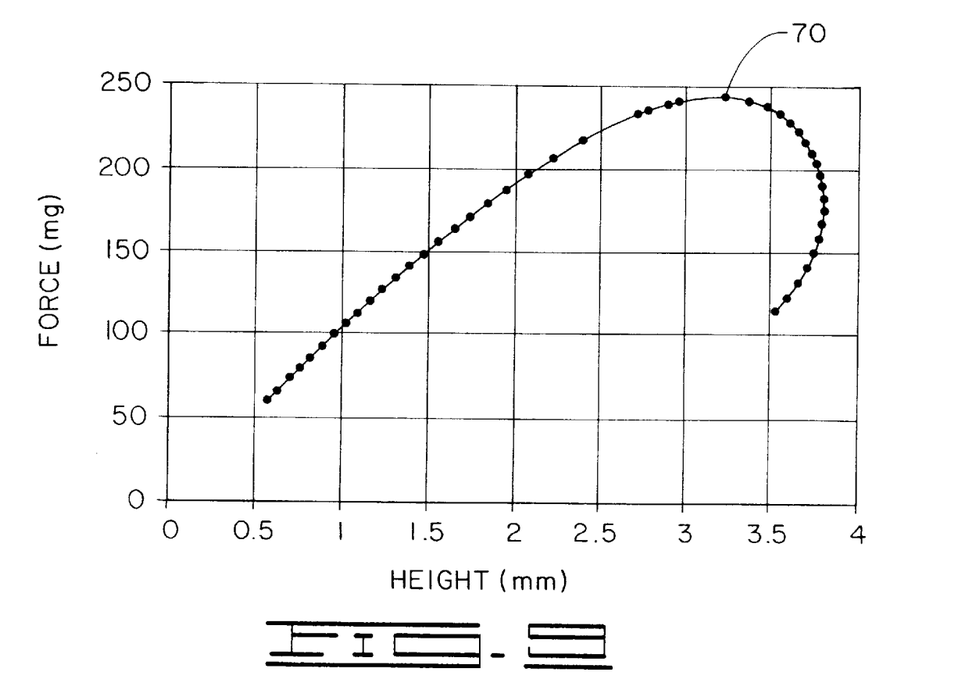
FIG. 9 presents a graph of experimental results obtained by plotting height versus weight (or force) and is illustrative of the typical curve obtained from measuring surface tension using the method given herein and the nature of the extremum obtained.

The method of measuring surface tension using the embodiment of the invention as shown in FIG. 5 is now described. Initially, a liquid sample 38 contained in a small sample cell 64 setting on the moveable stage 52 is positioned below the probe 32. The probe 32 is positioned vertically so that there is a gap of up to 2 cm. between the lower end of the probe 32 and the surface 42 of the sample liquid 38. Moveable stage 52 is slowly raised using the z adjustment means 58 until the sample liquid 38 contacts the lower end of the probe 32. Moveable stage 52 continues to be raised, thus moving the probe 32 into sample liquid 38 until a sufficient length of small diameter section 30 on the second end of probe 32 is wetted. Probe 32 must then be concentrically centered in small sample cell 64. This is accomplished by moving probe 32 incrementally back and forth in a horizontal direction using the x-adjustment means 60 until a maximum value of weight is located. Then probe 32 moved incrementally back and forth in a direction perpendicular to the preceding movement using the y-adjustment means 62 until a maximum value of weight is located; this procedure of finding the maximum weight is called zeroing or taring. After taring, the moveable stage 52 supporting the sample liquid 38 is slowly lowered using the z-adjustment means 58. By use of a micrometer, cathetometer, encoder, or other device associated with the moveable stage 52 which will measure height relative to the point at which the probe 32 just contacts the surface 42 of the sample liquid 38, a weight vs. height plot similar to that shown in FIG. 9 is obtained. As is apparent from the plot in FIG. 9, the position corresponding to maximum force 70 exerted by the surface tension of the sample liquid 38 can be determined quite accurately by alternatively raising and lowering the liquid cell 64, so that the extremum is approached both from below and above. Only the weight change at maximum pull must be determined in order to calculate the surface tension, provided that the gravitational constant, the density of the liquid, diameter of the probe 32, and inside diameter of the small sample cell 64 are known. This method may also be used when large sample cell 40 is used in lieu of small sample cell 64, in which case the taring step is not necessary since probe 32 is not in close proximity with the interior wall of sample cell 40 and the adjustment factor is negligible.

Figure 8:
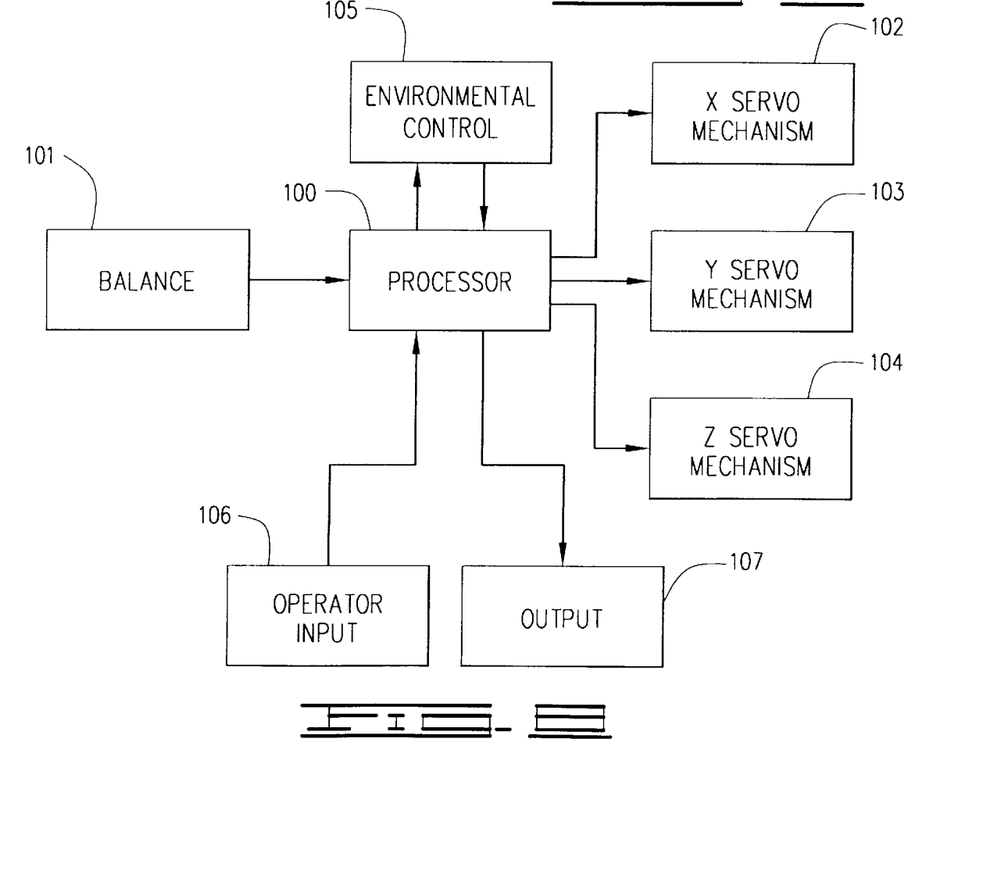
FIG. 8 presents a functional block diagram illustrating the configuration of an automated apparatus for measuring surface tension using the inverted vertical pull rod method.

This method, utilizing any of the embodiments described herein can be readily modified for automatic or semi-automatic operation, as shown in FIG. 8. A computer processor 100 is used for standard instrumentation of a top-loading balance 101 which provides continuous weight measurements while simultaneously controlling the height of the moveable stage using a z-servo mechanism 103 in the form of a stepper motor or similar device capable of being controlled automatically, with relative height measurements accurate to 1 $\mu$m. The processor 100 can also perform calculations for the correction factor necessary when measuring using small sample sizes, as well as the basic surface tension calculation. The environment control 105 is used to control conditions affecting the sample, such as temperature or paddles for maintaining the liquid in a mixed state. The user enters through the operator input device 106 (consisting of keyboard, computer mouse, touch screen menu selection, or similar method) parameters required by the processor software, such as the size of the probe, size of the container, and nature of the liquid being measured. Weight and height changes are monitored and controlled continuously in the feedback loop formed by the balance 101 and the z-servo mechanism 103 as, in one embodiment, the liquid sample is driven upward to contact the probe and then withdrawn until the maximum pull is exceeded or, in another embodiment, the probe is driven downward to contact the liquid sample and then withdrawn until maximum pull is exceeded. Multiple determinations of the maximum pull can be made thereby. All of the logical steps required in programming the entire measurement cycle can be made from knowledge of the observed weight at known times, for the known (predetermined) speed and direction of the z-servo mechanism 103. An output device 107 such as a cathode ray tube can be used to monitor the process by presenting in real-time plots of height versus weight. The reproducibility of repetitive measurements of the maximum pull in a single run and between runs is excellent, permitting determination of surface tension to within 0.03 mN m$^{-1}$, even with a balance 101 only accurate to the nearest milligram. The small sample method, previously described, requires an additional centering step prior to surface tension measurements, which involves positioning of the probe in the horizontal plane through the x-servo mechanism 102 and the y-servo mechanism 104 in order to center the probe within the small sample container. This zeroing or taring procedure involves moving the probe back in forth in both directions while observing the reading from the balance 101 until maximum force or pull (i.e. maximum weight) is achieved. Such a taring procedure is only possible if the probe, as described herein, is rigidly fixed to the movement mechanism so that capillary action of the sides of the container are overcome.

In summary, two major advantages accrue to using the invention with smaller liquid vessels. First, surface tensions can be measured for quite small liquid samples (well below 1 milliliter). Second, the measured surface effect (maximum weight) can exceed by 50% or more the effect determined with larger sample vessels.

While only a preferred embodiment has been illustrated and described, obvious modifications may be made within the scope of this invention and the following claims without substantially changing its functions. Accordingly, the scope of the invention should be determined not by the embodiments illustrated but by the appended claims and their legal equivalents.

The invention claimed is:

1. A method of measuring surface tension of a liquid, comprising the steps of:
   a. placing on a weight measuring means a container having a sample of a liquid, the surface tension of which is to be measured;
   b. recording the weight of the container and liquid, whereby a tare weight value is established;
   c. rigidly suspending a probe above the surface of the liquid, from an operating mechanism, whereby the operating mechanism orients the probe perpendicular to the surface of the liquid and controls bidirectional vertical motion of the probe;
   d. preparing for measuring surface tension by lowering the probe into the liquid using the operating mechanism until the lower surface and vertical sides of the probe are thoroughly wetted by the liquid;
   e. vertically raising the probe using the operating mechanism in incremental steps while maintaining the integrity of the meniscus around the probe;
   f. recording the weight of the container and liquid at each incremental step; and
   g. comparing the weight with the weight obtained during the previous incremental step until a minimum weight is obtained, whereby the minimum weight corresponds to maximum pull of the liquid on the probe.

2. The method of measuring surface tension of a liquid described in claim 1, further comprising a verification step comprising:

a. continuing raising the probe without breaking the meniscus of the liquid sample until one or more additional measurements are obtained;
   b. vertically lowering the probe in incremental steps using the operating mechanism;
   c. recording the weight of the container and liquid at each incremental step;
   d. comparing the weight with the weight obtained during the previous incremental step until a minimum weight is obtained; and
   e. comparing the value obtained by raising the probe with the value obtained by lowering the probe to verify that the same extremum is obtained.

3. The method of measuring surface tension of a liquid described in claim 1, further comprising the step of calculating surface tension, using as the force on the probe the difference between the tare weight and the minimum weight.

4. The method of measuring surface tension of a liquid described in claim 1, further comprising the preparation step of:
   a. moving the container bidirectionally and horizontally until a maximum value of weight is detected;
   b. positioning the probe at the point at which a maximum value of weight is detected;
   c. moving the container bidirectionally and horizontally in a direction perpendicular to the direction chosen previously; and
   d. positioning the probe at the point at which a maximum value of weight is detected.

5. A method of measuring surface tension of a liquid, comprising the steps of:
   a. placing on the balance pan of a top-loading balance a probe supported by a direction converter, said direction converter comprising a base resting on the balance pan, said base supporting a curved rod having a first end which is fixedly attached to said base and second end of which is a point of fixed attachment for the attachment end of the probe, the curvature of said curved rod orienting the measurement end of the probe fixedly and downwardly so that the probe is suspended in a direction normal to the plane of the balance pan;
   b. recording the weight of the probe and direction converter, whereby a tare weight value is established;
   c. placing a container holding the liquid for which a surface tension value is to be obtained on an operating mechanism, whereby the operating mechanism orients the container below the probe and controls bidirecitonal vertical motion of the container;
   d. preparing the probe for measurement by raising the container using the operating mechanism until the lower surface and vertical sides of the probe means are thoroughly wetted by the liquid in the container;
   e. vertically lowering the container and liquid in incremental steps using the operating mechanism while maintaining the integrity of the meniscus around the probe;
   f. recording the weight of the probe and direction converter at each incremental step; and
   g. comparing the weight with the weight obtained during the previous incremental step until a maximum weight is obtained, whereby the maximum weight corresponds to maximum pull of the liquid on the probe and direction converter.

6. The method of measuring surface tension of a liquid described in claim 5, further comprising the step of calculating surface tension force, using as the force on the probe the difference between the tare weight and the maximum weight.

7. The method of measuring surface tension of a liquid described in claim 5, further comprising the preparation step of:
   a. moving the container bidirectionally and horizontally until a maximum value of weight is detected;
   b. positioning the probe at the point at which a maximum value of weight is detected;
   c. moving the container bidirectionally and horizontally in a direction perpendicular to the direction chosen previously; and
   d. positioning the probe at the point at which a maximum value of weight is detected.

8. An apparatus for measuring surface tension of a liquid, said apparatus comprising
   a. a container confining the liquid, the container supported by a top-loading balance having a balance pan;
   b. a probe having an attachment end and a downwardly oriented measurement end;
   c. an operating mechanism independent of the top-loading balance, the attachment end of the probe being connected to the operating mechanism, the probe being vertically oriented over the surface of the liquid with the centerline axis between the attachment end and the measurement end being perpendicular to the surface of the liquid, the operating mechanism providing upward and downward movement to the measurement end of the probe and controlling the vertical distance between the measurement end and the surface of the liquid, whereby the force exerted on the probe is measured as the probe is alternately immersed in the liquid and withdrawn from the liquid.

9. The apparatus as described in claim 8, wherein the operating mechanism comprises a micrometer fixedly mounted in a vertical orientation on a stable platform and perpendicular to the surface of the liquid, the micrometer having a downwardly positioned spindle for fixed connection with the attachment end of the probe so that the measurement end is constrained from lateral movement, the micrometer being positioned in such proximity to the surface of the liquid such that the probe is sufficiently immersed in the liquid when the micrometer is extended to its maximum travel and not in contact with the liquid when the micrometer is collapsed to its minimum travel.

10. The apparatus as described in claim 8, wherein the operating mechanism comprises a moveable stage supporting directional converter consisting of a base providing stable support for a curved rod having a first end fixedly attached to the base and a second end to which the attachment end of the probe is connected, the curvature of said curved rod downwardly orienting the measurement end of the probe so that the centerline of the probe is perpendicular to the surface of the liquid, whereby upward and downward movement of the moveable stage results in upward and downward movement of the measurement end of the probe.

11. The apparatus as described in claim 8, wherein the operating mechanism further comprises a first means for bidirectional movement in a first horizontal direction and a second means for bidirectional movement in a second horizontal direction, the second horizontal direction being perpendicular to the first horizontal direction, whereby the position of the probe can be adjusted in a horizontal plane relative to the container without movement of the container.

12. The apparatus as described in claim 8, wherein the probe is rigidly fixed so as to prevent lateral movement of the measurement end.

13. The apparatus as described in claim 12, wherein the probe has a solid cylindrical measurement end with the cylindrical plane perpendicular to the centerline axis of the probe.

14. The apparatus as described in claim 13, wherein the container has an opening which is cylindrical in shape.

15. The apparatus as described in claim 14, wherein both the probe and the container are configured so that, when the measurement end of the probe is centrally positioned with and in contact with the liquid confined by the container, the distance between any point on the circumference of the measurement end of the probe and the interior wall of the container is at least 1 millimeter and at most 2 centimeters.

16. An apparatus for measuring surface tension of a liquid, said apparatus comprising
   a. a container confining the liquid;
   b. a probe having an attachment end and a measurement end;
   c. A top-loading balance having a balance pan, the balance pan supporting a directional converter, the directional converter consisting of a base resting on the balance pan, the base providing stable support for a curved rod having a first end fixedly attached to the base and a second end to which the attachment end of the probe is connected, the curved rod having a curvature which downwardly orients the measurement end of the probe so that the probe is positioned above the surface of the liquid and so that the centerline between the measurement end and attachment end is perpendicular to the surface of the liquid;
   d. an operating mechanism independent of the top-loading balance and supporting the container thereon, the operating mechanism imparting upward and downward movement to the container and controlling thereby the vertical distance between the measurement end of the probe and the surface of the liquid through movement of the container, whereby the force exerted on the probe is measured as the probe is alternately immersed in the liquid and withdrawn from the liquid.

17. The apparatus as described in claim 16, wherein the operating mechanism further comprises a first means for bidirectional movement in a first horizontal direction and a second means for bidirectional movement in a second horizontal direction, the second horizontal direction being perpendicular to the first horizontal direction, whereby the position of the container can be adjusted in a horizontal plane relative to the probe without movement of the probe.

18. The apparatus as described in claim 16, wherein the probe is rigidly fixed so as to prevent lateral movement of the measurement end.

19. The apparatus as described in claim 18, wherein the probe has a solid cylindrical measurement end with the cylindrical plane perpendicular to the centerline axis of the probe.

20. The apparatus as described in claim 19, wherein the mouth of the container is circular in shape.

21. The apparatus as described in claim 20, wherein both the probe and the container are configured so that, when the measurement end of the probe is centrally positioned with and in contact with the liquid confined by the container, the distance between any point on the circumference of the measurement end of the probe and the interior wall of the container is at least 1 millimeter and at most 2 centimeters.

* * * * *